United States Patent [19]

Montagna et al.

[11] 4,280,881

[45] Jul. 28, 1981

[54] SEPARATING INDENE FROM UNSATURATED ALKYLAROMATICS

[75] Inventors: John C. Montagna, O'Hara Township, Allegheny County; Robert D. Galli, New Kensington, both of Pa.; John Freel, Parker, Colo.

[73] Assignee: Gulf Research & Development Company, Pittsburgh, Pa.

[21] Appl. No.: 165,381

[22] Filed: Jul. 2, 1980

[51] Int. Cl.$^3$ .......................... B01D 3/40; C07C 7/08
[52] U.S. Cl. .......................................... 203/51; 203/57; 203/58; 203/71; 585/807; 585/808; 585/857; 585/864; 585/865
[58] Field of Search .................. 203/58, 57, 51, 60, 203/71; 585/807, 808, 833, 856, 857, 860, 864, 865

[56] References Cited

U.S. PATENT DOCUMENTS

| | | | |
|---|---|---|---|
| 2,228,789 | 1/1941 | Soday | 203/99 |
| 2,874,097 | 2/1959 | Schwoegler et al. | 203/58 |
| 2,996,438 | 8/1961 | Schwoegler et al. | 203/43 |
| 3,018,228 | 1/1962 | Cornell | 203/58 |
| 3,132,078 | 5/1964 | Backlund | 203/58 |
| 3,210,259 | 10/1965 | Cornell et al. | 203/58 |
| 3,647,900 | 3/1972 | Rozman | 203/57 |
| 3,723,256 | 3/1973 | Thompson | 585/857 |

*Primary Examiner*—Wilbur L. Bascomb, Jr.
*Attorney, Agent, or Firm*—Deane E. Keith; Forrest D. Stine; Donald L. Rose

[57] ABSTRACT

Indene is separated from close boiling, olefinically unsaturated alkylaromatic compounds by extractive distillation. For example, indene is separated from trans-β-methylstyrene, and from 2-, 3- and 4-methylstyrene by extractive distillation using 1-methyl-2-pyrrolidone as the extracting agent.

13 Claims, No Drawings

4,280,881

SEPARATING INDENE FROM UNSATURATED ALKYLAROMATICS

SUMMARY OF THE INVENTION

This invention relates to a process of separating indene from close boiling aromatic compounds by extractive distillation, and more particularly it relates to the separation of indene from close boiling monoolefinically unsaturated alkylaromatic compounds by extractive distillation.

DESCRIPTION OF THE INVENTION

Mixtures of close boiling aromatic compounds are produced in large quantities in various industrial and petroleum refinery operations. Where the scale of manufacture is very large, the total amount of the individual components in the mixture can be large even though the relative amount of a specific component is small. This is particularly true in the industrial pyrolysis of petroleum fractions, such as the naphthas and gas oils, for the production of ethylene and other low boiling components.

The pyrolysis of these higher boiling petroleum fractions results in a complex by-product liquid mixture of many dozens of compounds including a six to ten carbon, predominately aromatic component. Rather than using this entire liquid by-product as a fuel, it would be desirable individually to separate out those constituents which have a substantial commercial utility. However, due to the occurrence of many isomers and analogs having boiling points close to the desired compounds, clear separation of many of the individual compounds by distillation has heretofore been difficult or impossible.

The separation of olefinically unsaturated alkylaromatic compounds from close boiling saturated alkylaromatics, such as o-vinyltoluene from o-ethyltoluene and indene from indane, by extractive distillation using pyrrolidones is described in U.S. Pat. No. 3,210,259. However, the separation of mono-olefinically unsaturated alkylaromatic compounds from other mono-olefinically unsaturated alkylaromatic compounds is not disclosed.

We have now surprisingly discovered that certain polar compounds can be used for the separation of indene from mixtures containing different close boiling aromatic mono-olefins, such as the vinyltoluenes and trans-$\beta$-methylstyrene by extractive distillation. Thus, we have discovered that when the polar compound is present, it surprisingly associates itself with one of the olefinic compounds, indene, in some manner to hold it back and permit the other olefinic compounds, such as trans-$\beta$-methylstyrene and the vinyltoluenes, to be recovered in the vapor phase. In short, the polar solvent, surprisingly increases the relative volatility of various aromatic mono-olefins, including the vinyltoluenes and trans-$\beta$-methylstyrene, with respect to indene, a different aromatic mono-olefin.

The polar compounds which we find useful as an agent in the extractive distillation are oxygen-containing, nitrogen-containing and sulfur-containing polar compounds having boiling points within a desired range. This class of polar compounds includes sulfolane, 2-pyrrolidone, the N-lower alkyl-2-pyrrolidones such as N-methyl-2-pyrrolidone, $\gamma$-butyrolactone, ethylene carbonate, tetramethylene sulfoxide, the di-lower alkyl sulfoxides such as dimethyl sulfoxide, $\epsilon$-caprolactam, and the like.

The solvent not only enhances the relative volatility of the olefinic components undergoing separation from the indene, but also it possesses a boiling point within an optimum range. That is, the boiling point of the extraction solvent should be between about 190° and about 300° C., and preferably between about 195° and about 250° C. If the boiling point of the solvent is below that of indene, the solvent will leave the distillation column with the vapor and as a result fail to perform its function of holding back the indene. If the solvent's boiling point is too close to that of indene, it will perform its function but will itself be difficult to separate from the indene. And as the boiling point of the solvent becomes high, it tends to separate in the column downwardly from the indene thereby also losing its effectiveness. Additionally, solvents with boiling points excessively higher than indene have the tendency of imposing higher heat loads on the distillation because of the higher heats of vaporization and higher heat capacities, which characteristics are typical of the higher boiling solvents.

This process can be used to separate indene from a mixture containing other mono-olefinically unsaturated alkylaromatic compounds having boiling points close to indene regardless of the source of the mixture. A particularly rich potential source of indene is the pyrolysis gasoline stream resulting from the pyrolysis of heavier hydrocarbons including naphtha, gas oil and the like obtained as a by-product in the production of gaseous olefins. This pyrolysis gasoline, which is a mixture of paraffinic, aromatic and mixed paraffinic-aromatic hydrocarbons having between about five and about ten carbon atoms, generally contains several percent indene.

In order to more effectively use the extractive distillation procedure of the instant invention to recover the indene from pyrolysis gasoline or any similar mixture, it is desirable to concentrate in indene by ordinary fractional distillation into an indene-rich concentrate. This can be accomplished in two stages in which a light fraction boiling lower than indene is taken off in the first stage. The bottoms containing the indene is then fractionated in the second stage at more rigorous conditions to obtain the indene-rich concentrate as the overhead fraction, which is thereby separated from the higher boiling elements remaining in the tower bottoms. This overhead indene-rich fraction, also containing a substantial quantity of both alkenylaromatic and alkylaromatic compounds having boiling points close to indene, is then ready for the extractive distillation. The relative amount of indene in this fraction will depend on a number of factors including the amount of indene in the pyrolysis gasoline itself and the efficiency of each of the concentrating distillation stages.

The extractive distillation can be used to recover indene from a mixture containing any amount of indene but it is preferred that the indene in the close boiling mixture undergoing extraction comprise at least about ten percent of the total quantity of the close boiling mixture and it is most preferred that the indene comprise at least about 25 percent in order to significantly improve the overall economics of the recovery procedure. Additionally, although any amount of the extractive solvent will benefit the separation, we prefer that the weight ratio of the extractive solvent to the close boiling mixture undergoing extraction be at least about 0.2:1 and most preferably at least about 1:1 up to a maximum preferred weight ratio of about 5:1 and most preferably a maximum of about 3:1.

The extractive distillation can be carried out at atmospheric pressure but it is preferred that this distillation be carried out at reduced pressure in order to reduce the operating temperature and thereby minimize the polymerization of the olefinic constituents present in the column. Therefore, an operating pressure from about 25 mm Hg up to 760 mm and higher can be used, but it is preferred that the operating pressure as measured at the top of the distillation column be between about 30 and about 100 mm Hg. Additionally, a suitable polymerization inhibitor can be used in the extractive distillation column.

DESCRIPTION OF PREFERRED EMBODIMENTS

Examples 1 and 2

N-methyl-2-pyrrolidone was used in the separation by extractive distillation of indene from two different concentrate fractions of close boiling components. The concentrates were obtained from a pyrolysis gasoline containing 12.2 percent indene in a mixture of paraffinic, aromatic and substituted aromatic hydrocarbons having from six to ten carbon atoms. The indene was concentrated into two products having somewhat different analyses as set out in Table I. The extractive distillations were carried out in a one-inch inner diameter column packed with coiled metal springs to a height of 50 inches. The distillations were conducted at a ratio of N-methyl-2-pyrrolidone to the concentrate of 1.1:1, using a reflux ratio in the column of 5:1 and a pressure at the top of the column of 76 mm Hg in the first example, and a reflux ratio of 10:1 and a pressure of 74 mm Hg in the second. The results are set out in Table I.

TABLE 1

| Component | Feed, wt. % Ex. 1 | Feed, wt. % Ex. 2 | Product, wt. % Ex. 1 | Product, wt. % Ex. 2 | B.P. °C. |
|---|---|---|---|---|---|
| pseudocumene | 1.7 | 7.7 | — | — | 169.4 |
| vinyltoluenes | 5.1 | 33.0 | — | 0.6 | 170-172.8 |
| hemimellitene | 3.4 | 3.9 | — | — | 176.1 |
| indane | 7.5 | 4.7 | 0.4 | 0.5 | 178 |
| trans-β-methylstyrene | 7.0 | 4.2 | 2.1 | 0.65 | 178 |
| 1,3-diethylbenzene | 1.4 | 0.7 | — | — | 181 |
| 1,2-diethylbenzene | 5.0 | 2.6 | 0.5 | 0.45 | 183.4 |
| indene | 58.2 | 31.5 | 95.4 | 95.0 | 182.6 |
| other | 10.7 | 11.7 | 1.6 | 2.8 | (1) |

(1) a mixture of compounds boiling lower than indene.

EXAMPLE 3

A series of organic polar compounds were tested to determine whether the compounds could increase the relative volatility between 3- and 4-methylstyrene and indene when compared with the relative volatility in the absence of the polar solvent. The relative volatilities determined from these experiments are set out in Table II. All data were obtained at a temperature of 90° C. by operating the single stage distillation at reduced pressure. The solvent to hydrocarbon weight ratio S/HC as listed in the table is based on the total quantity of solvent-free hydrocarbons initially present in the solution. The hydrocarbons were present in a 50/50 weight ratio except as otherwise noted. The relative volatilities obtained with mixtures of indene with indane and with 1,2,3-trimethylbenzene (1,2,3-T) are also listed for comparison since these compounds are also generally present in pyrolysis gasoline.

TABLE II

| Solvent | S/HC | methylstyrenes indene 3 and 4$^a$ | methylstyrenes indene trans-β | indane indene | 1,2,3-T indene |
|---|---|---|---|---|---|
| none | 0/1 | 1.41 | 1.09 | 1.17 | 1.21 |
| NMP | 0.5/1 | — | 1.14$^b$ | — | — |
| | 1/1 | 1.56 | 1.21$^b$ | 1.61$^c$ | 1.69 |
| γ-Butyrolactone | 1/1 | 1.65 | 1.17$^b$ | 1.49 | — |
| | 2/1 | 1.60 | 1.26$^b$ | 1.67 | — |
| Ethylene carbonate | 0.5/1 | 1.72 | — | — | — |
| | 1/1 | — | — | 1.85$^d$ | 2.04$^d$ |
| Sulfolane | 1.5/1 | 1.58$^d$ | — | 1.61 | 2.01$^d$ |
| Dimethyl sulfoxide | 1/1 | 1.61$^c$ | — | 1.61$^c$ | — |
| Tetramethylene sulfoxide | 1.5/1 | 1.59 | — | 1.56$^d$ | 1.69$^d$ |
| 2-Pyrrolidone | 1/1 | 1.51 | — | 1.44 | — |
| | 1.5/1 | 1.52 | — | 1.53 | — |
| ε-Caprolactam | 1/1 | 1.53$^d$ | — | 1.44$^d$ | 1.61$^d$ |
| | 2/1 | 1.52$^d$ | — | 1.51$^d$ | 1.70$^d$ |

$^a$ a mixture of about 60% 3- and 40% 4-methylstyrene.
$^b$ hydrocarbon component contained equal parts by weight of indene, trans-β-methylstyrene and cis-β-methylstyrene.
$^c$ hydrocarbon component contained equal parts by weight of indene, vinyltoluenes and indane.
$^d$ hydrocarbon component contained equal parts by weight of indene, vinyltoluenes, indane and 1,2,3-trimethylbenzene.

If the indene concentration in the bottoms product resulting from extractive distillation does not meet the desired goal, this indene-enriched product can be submitted to one or more additional extractive distillations until the desired degree of indene enrichment is obtained.

It is to be understood that the above disclosure is by way of specific example and that numerous modifications and variations are available to those of ordinary skill in the art without departing from the true spirit and scope of the invention.

We claim:

1. The method of separating indene in admixture with at least one close boiling mono-olefinically unsaturated aromatic compound by extractive distillation which comprises distilling said mixture comprising indene and at least one close boiling mono-olefinically unsaturated aromatic compound in the presence of at least one liquid oxygen-containing, sulfur-containing or nitrogen-containing organic polar compound having a boiling point at 760 mm Hg of between about 190° and about 300° C., recovering a vapor phase rich in said mono-olefinically unsaturated aromatic compound and recovering a bottoms fraction rich in indene and said organic polar compound.

2. The method of separating indene in admixture with at least one close boiling mono-olefinically unsaturated aromatic compound by extractive distillation in accordance with claim 1 in which the olefinically unsaturated aromatic compound includes at least one component selected from 2-methylstyrene, 3-methylstyrene, 4-methylstyrene, trans-β-methylstyrene, and mixtures thereof.

3. The method of separating indene in admixture with at least one close boiling mono-olefinically unsaturated aromatic compound by extractive distillation in accordance with claim 2 wherein the polar compound is sulfolane, 2-pyrrolidone, γ-butyrolactone, ethylene carbonate, tetramethylene sulfoxide, ε-caprolactam, an N-lower alkyl-2-pyrrolidone, a di-lower alkyl sulfoxide, or a mixture thereof.

4. The method of separating indene in admixture with at least one close boiling mono-olefinically unsaturated aromatic compound by extractive distillation in accordance with claim 1 in which the indene comprises at least about ten percent of said mixture.

5. The method of separating indene in admixture with at least one close boiling mono-olefinically unsaturated aromatic compound by extractive distillation in accordance with claim 1 in which the weight ratio of said organic polar compound to said mixture is between about 0.2:1 and about 5:1.

6. The method of separating indene in admixture with at least one close boiling mono-olefinically unsaturated aromatic compound by extractive distillation in accordance with claim 1 in which the boiling point of the organic polar compound is between about 195° and about 250° C.

7. The method of separating indene in admixture with at least one close boiling mono-olefinically unsaturated aromatic compound by extractive distillation in accordance with claim 3 in which the polar solvent is N-methyl-2-pyrrolidone.

8. The method of separating indene in admixture with at least one close boiling mono-olefinically unsaturated aromatic compound by extractive distillation in accordance with claim 3 in which the polar solvent is $\gamma$-butyrolactone.

9. The method of separating indene in admixture with at least one close boiling mono-olefinically unsaturated aromatic compound by extractive distillation in accordance with claim 3 in which the indene is recovered from said bottoms fraction by distillation.

10. The method of separating indene in admixture with at least one close boiling mono-olefinically unsaturated aromatic compound by extractive distillation in accordance with claim 3 in which said mixture includes 2-, 3-, or 4-methylstyrene or a mixture thereof.

11. The method of separating indene in admixture with at least one close boiling mono-olefinically unsaturated aromatic compound by extractive distillation in accordance with claim 3 in which said mixture includes trans-$\beta$-methylstyrene.

12. The method of separating indene in admixture with at least one close boiling mono-olefinically unsaturated aromatic compound by extractive distillation in accordance with claim 1 in which the indene comprises at least about 25 percent of said mixture.

13. The method of separating indene in admixture with at least one close boiling mono-olefinically unsaturated aromatic compound by extractive distillation in accordance with claim 1 in which the weight ratio of said organic polar compound to said mixture is between about 1:1 and about 3:1.

* * * * *